United States Patent [19]

Makino et al.

[11] Patent Number: 5,158,944

[45] Date of Patent: Oct. 27, 1992

[54] SOLID PHARMACEUTICAL PREPARATIONS OF ACTIVE FORM OF VITAMIN D3 OF IMPROVED STABILITY

[75] Inventors: Yuji Makino; Yoshiki Suzuki, both of Tokyo, Japan

[73] Assignee: Teijin Limited, Osaka, Japan

[21] Appl. No.: 601,775

[22] PCT Filed: Feb. 28, 1990

[86] PCT No.: PCT/JP90/00255

§ 371 Date: Oct. 31, 1990

§ 102(e) Date: Oct. 31, 1990

[87] PCT Pub. No.: WO90/09796

PCT Pub. Date: Sep. 7, 1990

[30] Foreign Application Priority Data

Mar. 1, 1989 [JP] Japan .................................. 1-46571

[51] Int. Cl.$^5$ ............................................. A61K 31/59
[52] U.S. Cl. .................................. 514/167; 514/960; 514/970
[58] Field of Search .................... 514/167, 960, 970

[56] References Cited

U.S. PATENT DOCUMENTS

| | | | |
|---|---|---|---|
| 2,195,596 | 4/1940 | Nitardy | 167/81 |
| 2,691,619 | 10/1954 | Havley et al. | 167/81 |
| 3,901,928 | 8/1975 | Hesse et al. | 260/397.2 |
| 3,932,615 | 1/1976 | Ito et al. | 424/80 |
| 4,069,321 | 1/1978 | Jones et al. | 424/236 |
| 4,308,264 | 12/1981 | Conway | 424/236 |
| 4,613,594 | 9/1986 | Baggiolini et al. | 514/167 |
| 4,617,297 | 10/1986 | Boris et al. | 514/167 |
| 4,652,405 | 3/1987 | Partridge et al. | 260/397.1 |
| 4,711,881 | 12/1987 | Ikekawa | 514/167 |
| 4,729,895 | 3/1988 | Makino | 424/465 |

FOREIGN PATENT DOCUMENTS

| | | |
|---|---|---|
| 0116755 | 8/1984 | European Pat. Off. . |
| 0191489 | 8/1986 | European Pat. Off. . |
| 51-128417 | 11/1976 | Japan . |
| 57-40414 | 3/1982 | Japan . |
| 57-40415 | 3/1982 | Japan . |
| 61-41351 | 9/1986 | Japan . |
| 62-48667 | 10/1987 | Japan . |
| 62-51948 | 11/1987 | Japan . |
| 63-46728 | 9/1988 | Japan . |
| 1081667 | 8/1967 | United Kingdom . |
| 1456618 | 11/1976 | United Kingdom . |

OTHER PUBLICATIONS

Remington's Pharmaceutical Sciences 15th Ed. Mack Pub. Co., Easton, Pa.
International Search Report.
"The Merck Index", 11th Edition, 1989, pp. 1578–1579, Rahway, N.J., US, Abstract Nos. 9928–9929: Vitamins $D_2$, $D_3$.

Primary Examiner—Frederick E. Waddell
Assistant Examiner—Diane Gardner
Attorney, Agent, or Firm—Sughrue, Mion, Zinn, Macpeak & Seas

[57] ABSTRACT

A pharmaceutical solid preparation of active form of vitamin $D_3$ of improved stability which comprises a composition of active form of vitamin $D_3$ dispersed in an excipient readily soluble in organic solvent and a basic substance.

As a basic substance, are cited sodium citrate, magnesium oxide or the like.

4 Claims, No Drawings

SOLID PHARMACEUTICAL PREPARATIONS OF ACTIVE FORM OF VITAMIN D3 OF IMPROVED STABILITY

The Field of the Art

The present invention relates to a solid pharmaceutical preparation of active form of vitamin $D_3$. Particularly, the present invention relates to a solid preparation of active form of vitamin $D_3$ of improved stability wherein the preparation is composed of an active form of vitamin $D_3$ composition containing active form of vitamin $D_3$ dispersed in an excipient readily soluble in organic solvent, and a basic substance.

The Background of the Invention

The compounds which are typified by $1\alpha$-hydroxycholealciferol, $1\alpha,25$-dihydroxychlolecalciferol or $1\alpha,24$-dihydroxycholecalciferol have been known as active forms of vitamin $D_3$ (Martin J. Calverley; Tetrahedron Vol. 43, No. 20, 4609–4619, 1987), and it has been clarified that these active forms of vitamin $D_3$ distribute, after being absorbed in the living body, in intestinal tracts, kidney, parathyroid gland and bone tissues and bind to the receptors to develop their pharmacological actions such as Ca absorption from intestinal tracts, increase of serum Ca level, secretory inhibition of parathyroid hormone or bone formation. Thus, the active forms of vitamin $D_3$ have been clinically applied to a variety of symptoms (hypocalcemia, tetany, bone ache, bone lesion, and so on) accompanied by dysbolism of vitamin D in chronic renal failure, hypoparathyroidism, vitamin D resistant rickets, and osteomalacia, as well as for treatment of osteoporosis.

These active forms of vitamin $D_3$ are chemically unstable to heat, light and oxygen and means such as refrigeration, light shading or replacement with an inert gas are required for storage of these vitamin $D_3$ themselves.

Therefore, it would be very useful that these active forms of vitamin $D_3$ are provided in the form of a stabilized preparation.

Conventionally, as a method for stabilizing these active forms of vitamin $D_3$ in the solid state, have been proposed the clathration of the vitamin $D_3$ with cyclodextrin by the present inventors (Japanese Patent Application Laidopen No. 128417/'76), the clathration with bile acids (Japanese Patent Publication No. 41351/'86), the complex formation with sterols (Japanese Patent Publication No. 51948/'87), the dispersion in polyvinyl pyrrolidone (Japanese Patent Publication No. 46728/'88), the formation of the outer layer containing an active form of vitamin $D_3$ and an excipient readily soluble in organic solvent, for example, polyvinyl pyrrolidone or hydroxypropyl cellulose on the inner layer comprising an excipient slightly soluble in organic solvent, for example, lactose or crystalline cellulose (Japanese Patent Publication No. 60007/'88) or the like.

The composition of the active form of vitamin $D_3$ is usually mixed with other components, for example, known excipient, lubricant, binder, colorant, antioxidant or the like, formed into a solid preparation, for example, tablets, hard shell capsules, granules, powders and used for medical purposes.

The solid preparation of active form of vitamin $D_3$ produced in such a manner has excellent stability for a long period of time under usual storage conditions, for example, at room temperature (at the ambient temperature indoor) and the tablets of $1\alpha$-hydroxycholecalciferol have been actually used over a wide range of the clinical fields.

The preparations are under suitable control, while they are in medical institution after being produced, further they are packed, thus their quality is guaranteed. After they are given to the patients, however, they are opened and taken out of the package, therefore, may be frequently exposed directly to unexpected drastic conditions, for example to high temperature and humidity. In the case of the preparations of active form of vitamin $D_3$, it has become possible that the preparation which stands the long-term storage at room temperature is provided by converting the markedly unstable vitamin $D_3$ itself into a stabilized composition by a variety of measures and techniques, but the reduction in the content of the active ingredient is unavoidable, when the composition is exposed to drastic conditions, for example, exposed to high temperature and humidity in the unpacked state.

THE SUMMARY OF THE INVENTION

Accordingly, it is an object of the present invention to provide a solid pharmaceutical preparation which causes no content reduction in the active ingredient, even when it is unpacked and exposed to high temperature and humidity.

The present invention is a solid pharmaceutical preparation of active form of vitamin $D_3$ which comprises a composition of active form of vitamin $D_3$ containing an active form of vitamin $D_3$ dispersed in an excipient readily soluble in organic solvent, and a basic substance.

THE DETAILED DESCRIPTION OF THE PREFERRED EMBODIMENTS

The present inventors have made intensive research on a solid pharmaceutical preparation of more improved stability with lowered content reduction in the active ingredient even under drastic conditions such as high temperature and humidity and have found that the addition of a basic substance to conventionally known composition of active form of vitamin $D_3$ can provide a solid pharmaceutical preparation of active form of vitamin $D_3$ which is stabilized under high temperature and humidity conditions.

In other words, the present inventors have made investigation, in detail, on the factors for stability of the solid pharmaceutical preparations of active form of vitamin $D_3$ and known the following matters:

(1) The active form of Vitamin $D_3$ needs to be stabilized in a composition such that it is dispersed in an excipient which is readily soluble in an organic solvent. However, while stabilization with other compounds is difficult to obtain, when Vitamin $D_3$ is directly mixed with excipients which are even only slightly soluble in ordinary organic solvents, for example, such excipients as crystalline cellulose or lactose, the Vitamin D compositions are no longer evenly dispersed, for example, such that the excipient is dispersed on the back face (See Japanese Patent Publication Nos. 41351/1986, 51948/1987, 46728/1988 and 60007/1988).

(2) Such an amount of active form of Vitamin $D_3$, dispersed in an excipient readily soluble in an organic solvent, is not reduced by high temperature or high humidity alone, but when both heat and humidity conditions exist, reduction in the active form of Vitamin $D_3$ occurs.

(3) Under high temperature and humidity conditions, the moisture can penetrate into the preparation having active form of vitamin $D_3$ dispersed in an excipient readily soluble in organic solvent.

(4) Under high temperature conditions, the penetrating moisture can dissolve the excipient readily soluble in organic solvent in a trace amount, though.

(5) As a result, the active form of vitamin $D_3$ in the solid preparation is in the state of an aqueous solution, under high temperature and humidity, microscopically together with the excipient readily soluble in organic solvent. Accordingly, the partial reduction of the content which is unavoidable under high temperature and humidity seems to be caused by the liability of the active form of vitamin $D_3$ in the state of an aqueous solution.

In the meantime, the present inventors studied the correlation between the decomposition rate of active form of vitamin $D_3$ which is solubilized in water with a surface active agent and the pH of the solution and observed that the decomposition rate is large in the low pH range, but the rate decreases, as the pH rises, shows the minimum value near 6.5 to 8.0 pH, then the rate is in a increasing tendency, as pH increases.

Thus, the present inventors measured the pH of the aqueous solution or suspension of the excipient readily soluble in water and found that PVP: about 4, HPC: about 5 to 6, HPMC: about 6, MC: about 5 to 6, sterols: 6, deoxycholic acid: about 5, all of them are weakly acidic, lower than the pH range at which active form of vitamin $D_3$ is most stable in water, that is, 6.5 to 8.0.

On the basis of these findings and observation, the present inventors thought that a stabilized solid pharmaceutical preparation of active form of vitamin $D_3$ could be provided without rapid content reduction of the active ingredient by adding another substance to the conventional composition of active form of vitamin $D_3$ having the active ingredient dispersed in an excipient readily soluble in organic solvent to keep the pH of the moisture at 6.5 to 8.0, even when a part of the active form of vitamin $D_3$ is solubilized in the moisture under high temperature and humidity.

At that time, the pH of aqueous solution or suspension of usual additives which can be added to solid preparations was examined and found to be starch: about 4.5 to 6.0, crystalline cellulose: about 5.5 to 6.5, lactose: about 4.0 to 6.0, mannitol: about 5.5 to 6.5, sucrose: about 7.0, gelatin: about 4.0 to 7.0, calcium phosphate: about 6.5, aluminum silicate: about 7.0 and kaolin: about 4.0 to 6.0. Thus, it was found that most of them cannot neutralize the weak acidity of the aqueous solution or suspension of the excipient readily soluble in organic solvent, while aluminum hydroxide gel, bentonite, magnesium aluminum silicate and others have neutralization ability, but they originally have high water content, consequently, the content of active form of vitamin $D_3$ in the solid preparation containing these additives was a little lowered, before exposure to high temperature and humidity. Thus, the inventors have known that the substance to be used as an additive for neutralization of a solid preparation of active form of vitamin $D_3$ must be (1) basic and (2) low in water content. Thereupon, they intensively sought the substances satisfying the two conditions and found that only basic substances can produce the solid preparation of active form of vitamin $D_3$ of improved stability and reached the present invention.

In the present invention, the excipient which is readily soluble in organic solvent is suitably polyvinyl pyrrolidone (PVP), hydroxypropylcellulose (HPC), hydroxypropylmethylcellulose (HPMC), methyl cellulose (MC), cholesterol, $\beta$-sitosterol, campesterol, deoxycholic acid or the like. Polyvinyl pyrrolidone (PVP), hydroxypropylcellulose (HPC), hydroxypropylmethylcellulose (HPMC) are more suitable among them.

According to the present invention, the active form of vitamin $D_3$ used is an active form of vitamin $D_3$ bearing a hydroxyl group in the 1$\alpha$-position, such as 1$\alpha$-hydroxycholecalciferol (1$\alpha$-OH-$D_3$), 1$\alpha$, 25-dihydroxycholecalciferol (1$\alpha$,25-(OH)$_2$-$D_3$), 1$\alpha$,24-dihydroxycholecalciferol (1$\alpha$,24-(OH)$_2$$D_3$), 1$\alpha$,24,25-trihydroxycholecalciferol (1$\alpha$,24,25-(OH)$_3$$D_3$), 1$\alpha$-hydroxy-24-oxocholecalciferol, 1$\alpha$, 25-dihydroxy-24-oxocholecalciferol, 1$\alpha$,25-dihydroxy-cholecalciferol-26,23-lactone, 1$\alpha$,25-dihydroxy-cholecalciferol-26,23-peroxylactone, 26,26,26,27,27,27-hexafluoro-1$\alpha$,25-dihydroxy-cholecalciferol, or an active form of vitamin $D_3$ bearing no hydroxyl group in the 1$\alpha$-position, such as 25-hydroxycholecalciferol (25-OH-$D_3$), 24-hydroxycholecalciferol (24-OH-$D_3$), 24-oxocholecalciferol, 24,25-dihydroxycholecalciferol (24, 25-(OH)$_2$-$D_3$), 25-hydroxy-24-oxo-cholecalciferol, 25-hydroxycholecalciferol-26,23-lactone, 25-hydroxycholecalciferol-26,23-hydroxycholecalciferol-26,23-peroxylactone or the like.

Among these active forms of vitamin $D_3$, 1$\alpha$-OH-$D_3$, 1$\alpha$,25-(OH)$_2$-$D_3$, 1$\alpha$,24-(OH)$_2$-$D_3$ and 1$\alpha$,25-(OH)$_2$-$D_3$-26,23-lactone are preferred.

The basic substance used in the present invention is defined as a compound showing a pH higher than 7, preferably higher than 7.5, when it is dissolved or suspended in water. Examples of the basic substance include preferably sodium citrate, calcium hydroxide, calcium oxide, magnesium oxide, potassium carbonate, magnesium carbonate, sodium carbonate, sodium hydrogen carbonate, disodium hydrogen phosphate, dipotassium hydrogen phosphate, trisodium phosphate, potassium pyrophosphate, sodium pyrophosphate, particularly preferably sodium citrate, magnesium oxide, potassium carbonate, magnesium carbonate, sodium carbonate, disodium hydrogen phosphate, dipotassium hydrogen phosphate, trisodium phosphate and sodium pyrophosphate.

The amount of the excipient readily soluble in organic solvent according to the present invention is preferably 1 to 5,000,000 fold, particularly preferably 10 to 1,000,000 fold weight of the active form of vitamin $D_3$.

The amount of the basic substance used in the present invention corresponds to that in which the pH of the moisture penetrating in the solid preparation containing the composition according to the present invention under high temperature and humidity is kept near about 6.5 to 8.0, and cannot be determined simply, because it depends upon the amount of the excipient readily soluble in organic solvent, the composition of active form of vitamin $D_3$ according to present invention, additionally the amounts and properties of known additives for making solid preparations, for example, extender, binder, disintegrator, but roughly it is about 1 to 5,000,000 folds, preferably 10 to 1,000,000 folds based on the active form of vitamin $D_3$.

The composition of active form of vitamin $D_3$ dispersed in an excipient readily soluble in organic solvent is obtained by mixing, with thoroughly stirring, an active form of vitamin $D_3$ and an excipient readily soluble in organic solvent in an solvent which can dissolve both of them, such as an alcohol solvent, for example, methanol. ethanol or propanol, then distilling off the solvent under reduced pressure or cooling the mixture of precipitating the product with water or a saline solution.

More preferably, the outer layer which is composed of an active form of vitamin $D_3$ and an excipient readily soluble in organic solvent is formed on an inner layer which is composed of an excipient slightly soluble in organic solvent. In other words, the particles or fine particles slightly soluble in organic solvent is used as an inner layer and the surface of the inner layer may be adhered to or coated with active form of vitamin $D_3$ and an excipient readily soluble in organic solvent. In this concern, the excipient which is slightly soluble in organic solvent is crystalline cellulose, starch, casein, cyclodextrin, lactose, hydroxypropylstarch, dextrin or gelatin. The basic substance according to the present invention may be used as an excipient slightly soluble in organic solvent for the inner layer.

The organic solvent used in this concern is an alcohol solvent such as methanol, ethanol, propanol, a halogenated hydrocarbon, such as dichloromethane or chloroform, an ether solvent such as diethyl ether. An alcoholic solvent such as methanol or ethanol is particularly preferred. The organic solvent may be a mixture of 2 or more solvents. The active form of vitamin $D_3$ and an excipient readily soluble in organic solvent are dissolved in such an organic solvent. The amount of the organic solvent used is usually 1 to 1,000 folds, preferably 1 to 100 folds the weight of the excipient readily soluble in organic solvent.

Then, an excipient slightly soluble in organic solvent is added. At this time, the excipient is uniformly dispersed in the organic solvent. After thoroughly stirring, the organic solvent is removed by a suitable method such as with heat under reduced or normal pressure or by spray-drying.

Through such operations, the subject composition is obtained by forming an outer layer containing an active form of vitamin $D_3$ and an excipient readily soluble in organic solvent on the inner layer of another excipient slightly soluble in an organic solvent.

The composition of active form of vitamin $D_3$ dispersed in an excipient readily soluble in organic solvent and a basic substance according to the present invention are directly mixed to give the pharmaceutical preparation of active form of vitamin $D_3$ according to the present invention. Additionally, when needed, other excipients, binders, disintegrators, antioxidant, antioxidant enhancer, colorants, lubricants may be combined to give the solid preparations such as tablets, hard capsules, granules, powders or the like.

The excipients used, when needed, in the production of the preparations are, for example, starch, crystalline cellulose, dextrin, lactose, mannitol, sorbitol, anhydrous calcium phosphate, sucrose, talc (naturally occurring magnesium silicate hydrate), kaolin, precipitated calcium carbonate, sodium chloride, titanium oxide, lightweight anhydrous silicic acid; the binders are, for example, starch, dextrin, tragacanth gum, gelatin, polyvinyl pyrrolidone, polyvinyl alcohol, hydroxypropylcellulose, crystalline cellulose, hydroxypropylmethylcellulose, ethyl cellulose, carboxymethylcellulose, Arabic gum or the like; disintegrators are, for example, starch, crystalline cellulose, carboxymethylcellulose calcium, agar-agar powder or the like; the antioxidant is, for example, butyl hydroxytoluene (BHT), propyl gallate, butyl hydroxyanisole (BHA), lecithin, α-tocopherol, hydroquinone, octyl gallate, dodecyl gallate, isoamyl gallate, nordihydroguaialetic acid, guaiac resin, α-naphthylamine, ethyl protocathecuate (EPG), ascorbic acid stearate ester, ascorbic acid palmitate, cysteine hydrochloride, sodium ascorbic stearate, thioglycerol, thiosorbitol or the like; the antioxidant enhancer is, for example, dihydroxyethylglycine, ethylenediaminetetraacetic acid, glycerol, phenylalanine, sorbitol, tryptophan or the like; the colorant is, for example, tar pigments (synthetic organic food additives) of which the use in medicines is approved by the Welfare Ministry; and the lubricant is, for example, talc, starch, magnesium and calcium stearate, boric acid, paraffin, cocoa butter, macrogol, leucine, sodium benzoate and the like. A known process is applied to produce tablets, capsules, granules or the like using these additive. Thus, according to the present invention, a pharmaceutical preparation of active form of vitamin $D_3$ of improved stability is provided and the significant is great.

The present invention will be illustrated in more detail, by the following examples. The present invention, however, is never limited with these examples.

EXAMPLE 1

One mg of 1α-OH-$D_3$ was dissolved in 1 ml of ethanol to form a solution and the solution was added to the solution of 1. g polyvinyl pyrrolidone (molecular weight: about 40,000) in 10 ml of ethanol, then the mixture was stirred for 10 minutes. Additionally, 2 g of anhydrous lactose (Japanese Standards of Pharmaceutical Ingredients, 1989) was added to the solution. Then, the ethanol was evaporated off under reduced pressure to dryness to give 2.96 g of the reaction product. The content of 1α-OH-$D_3$ was 0.033% in the reaction mixture.

The reaction product was crushed with a coffee mill, sieved through 80 mesh screen to provide the 1α-OH-$D_3$ composition. Disodium hydrogen phosphate was mixed with the resultant composition in the same amount of the composition to give the solid pharmaceutical preparation of 1α-OH-$D_3$ of uniform dispersion (example 1). The solid preparation was placed on a petri dish and kept in a thermo-hygrostat which was controlled to 40° C. and 75% relative humidity so that the residual percentage of 1α-OH-$D_3$ was examined with the passage of time. As a control, the single composition of 1α-OH-$D_3$ (Comparison 1) was placed on a Petri dish and stored in a thermo-hygrostat at 40° C. and 75% relative humidity. The time courses of the residual rate of 1α-OH-$D_3$ are shown in Table 1 in the solid preparation according to the present invention and the single composition. As shown clearly in the table, the solid preparation is more stable than the composition as a control under high temperature and humidity.

TABLE 1

| Conditions | time (after) | solid preparation (Example 1) | composition (Comparison 1) |
|---|---|---|---|
| 1α-OH-$D_3$ residual rate (%) at 40° C. and 75% RH | 7 days | 97 | 89 |
| | 14 days | 95 | 73 |
| | 30 days | 91 | 67 |

EXAMPLES 2 THROUGH 7

Instead of polyvinyl pyrrolidone as an excipient readily soluble in organic solvent in Example 1, the excipients given in Table 2 were used, and instead of anhydrous lactose in Example 1, excipients shown in Table 2 were employed, additionally, instead of 1α-OH-D$_3$ in Example 1, the active forms of vitamin D$_3$ were used to prepare the compositions of active form of vitamin D$_3$. The compositions were combined with basic substances given in Table 2 instead of disodium hydrogen phosphate in Example 1 to provide solid preparations of active form of vitamin D$_3$ according to the present invention and their stabilities at 40° C. and 75% relative humidity were compared with their corresponding single compositions as a control, respectively. Further, in Example 6, in addition of Comparison 6-1 (not containing the basic substance), comparison 6-2 (including citric acid) was also compared on its stability. The results are given in Table 2 and any solid preparations according to the present invention are clearly more stable under high temperature and humidity.

(a) an active form of vitamin D$_3$ dispersed in an excipient readily soluble in an organic solvent; and
(b) a basic substance,
wherein the excipient readily soluble in an organic solvent is at least one selected from the group consisting of polyvinyl pyrrolidone, hydroxypropylcellulose, hydroxypropylmethylcellulose, methylcellulose, cholesterol, β-sitosterol, campesterol, and deoxycholic acid,
wherein the basic substance is at least one selected from the group consisting of sodium citrate, calcium hydroxide, calcium oxide, magnesium oxide, potassium carbonate, magnesium carbonate, sodium carbonate, sodium hydrogen carbonate, disodium hydrogen phosphate, dipotassium hydrogen phosphate, trisodium phosphate, potassium pyrophosphate, and sodium pyrophosphate, and
wherein the base substance is present in the solid preparation in an amount of 1 to 5,000,000 times the amount of the active form of vitamin D$_3$.

2. A pharmaceutical solid preparation of active form of vitamin D$_3$ according to claim 1, wherein the active

TABLE 2

| | Compositions of active form of vitamin D$_3$ | | | | Residual rate (%) of active form of vitamin D$_3$ at 40° C. and 75% RH after | | |
|---|---|---|---|---|---|---|---|
| No. | Excipient readily soluble in organic solvent | Excipient slightly soluble in organic solvent | Active forms of vitamin D$_3$ | Basic substance | 7 days | 14 days | 30 days |
| Example 2 | polyvinyl pyrrolidone | anhydrous lactose | 1α,24-(OH)$_2$-D$_3$ | Na$_2$HPO$_4$ | 98 | 95 | 93 |
| Comparison 2 | " | " | " | none | 91 | 83 | 71 |
| Example 3 | polyvinyl pyrrolidone | crysta. cellulose | 1α-OH-D$_3$ | Na$_2$HPO$_4$ | 100 | 99 | 94 |
| Comparison 3 | " | " | " | none | 88 | 81 | 69 |
| Example 4 | hydroxypropylcellulose | anhydrous lactose | 1α-OH-D$_3$ | Na$_2$CO$_3$ | 96 | 96 | 91 |
| Comparison 4 | " | " | " | none | 90 | 81 | 68 |
| Example 5 | hydroxypropylcellulose | crysta. cellulose | 1α,24-(OH)$_2$-D$_3$ | NaHCO$_3$ | 98 | 95 | 93 |
| Comparison 5 | " | " | " | none | 91 | 79 | 72 |
| Example 6 | hydroxypropylmethylcellulose | lactose | 1α-OH-D$_3$ | Na citrate | 97 | 93 | 92 |
| Comparison 6-1 | " | " | " | none | 88 | 80 | 77 |
| Comparison 6-2 | " | " | " | citric acid | 73 | 68 | 54 |
| Example 7 | deoxycholic acid | lactose | 1α,24-(OH)$_2$-D$_3$ | CaO | 95 | 95 | 94 |
| Comparison 7 | " | " | " | none | 90 | 71 | 63 |

EXAMPLE 8

The 1α-OH-D$_3$ composition in Example 1 (0.75 part by weight) was thoroughly mixed with 72.25 parts by weight of anhydrous lactose and 10 parts by weight of disodium hydrogen phosphate. Then, 1 part by weight of magnesium stearate was admixed to the mixture, and they were tableted with a Erweka single tableter into tablets of 7 mm diameter and about 1.8 mm thickness. The weight of each tablet was about 84 mg and about 0.25 μg of 1α-OH-D$_3$ every tablet.

POSSIBILITY OF INDUSTRIAL UTILIZATION

The present invention can provide solid pharmaceutical preparations of active form of vitamin D$_3$ in which the content of the active ingredient is not lowered even when they are exposed to the conditions of high temperature and humidity and becomes possible to utilize them for amelioration of symptoms caused by vitamin D dysbolism and treatment for osteoporosis as a preparation of active form of vitamin D$_3$ of improved stability

We claim:

1. A pharmaceutical solid preparation of an active form of vitamin D$_3$, comprising form of vitamin D$_3$ is at least one selected from the group consisting of 1α-hydroxycholecalciferol, 1α,25-dihydroxycholecalciferol, 1α, 24-dihydroxycholecalciferol, 1α, 24,25-trihydroxycholecalciferol, 1α-hydroxy-24-oxocholecalciferol, 1α, 25-dihydroxy-24-oxo-cholecalciferol, 1α, 25-dihydroxy-cholecalciferol-26,23-lactone, 1α, 25-dihydroxy-cholecalciferol-26,23-peroxylactone, 26,26,26,27,27,27-hexafluoro-1α, 25-dihydroxy-cholecalciferol, 25-hydroxycholecalciferol, 24-hydroxycholecalciferol, 24-oxocholecalciferol, 24,25-dihydroxycholecalciferol, 25-hydroxy-24-oxo-cholecalciferol, 25-hydroxycholecalciferol-26,23-lactone, and 25-hydroxycholecalciferol-26,23-peroxylactone.

3. A pharmaceutical solid preparation of active form of vitamin D$_3$ according to claim 1, wherein the amount of the excipient readily soluble in organic solvent is 1 to 5,000,000 times the amount of the active form of vitamin D$_3$.

4. A pharmaceutical preparation of an active form of vitamin D$_3$, comprising a solid preparation of an active form of vitamin D$_3$ according to claim 1 and a pharmaceutically acceptable carrier or diluent, wherein the pharmaceutical preparation is in the form of tablets, capsules or granules.

* * * * *